US00PP12829P2

(12) United States Plant Patent
Ravenscroft

(10) Patent No.: US PP12,829 P2
(45) Date of Patent: Aug. 6, 2002

(54) GERANIUM PLANT NAMED 'RAVPIL'

(75) Inventor: John Ravenscroft, NR. Nantwich (GB)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/643,899

(22) Filed: Aug. 22, 2000

(51) Int. Cl.[7] ..... A01H 5/00
(52) U.S. Cl. ..... Plt./324
(58) Field of Search ..... Plt./324

(56) References Cited

PUBLICATIONS

UPOV–ROM GTITM Computer Database, 2001/02, GTI Jouve Retrieval Software, citation for 'Ravpil'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Geranium plant named 'Ravpil', characterized by its medium green leaf color; mounded and prostrate growth habit; and dark purple-colored flowers.

2 Drawing Sheets

BACKGROUND OF THE INVENTION

The present Invention relates to a new and distinct cultivar of Geranium plant, botanically known as *Geranium cinereum,* and hereinafter referred to by the cultivar name Ravpil.

The new Geranium was discovered by the Inventor in a controlled environment in Cheshire, United Kingdom, as a whole plant mutation of the *Geranium cinereum* cultivar Laurence Flatman, not patented, In June, 1989. Plants of the new Geranium have darker purple flowers than plants of the cultivar Laurence Flatman. Plants of the new Geranium typically have darker purple flowers than other Geraniums of this type known to the Inventor.

Asexual reproduction of the new cultivar by cuttings harvested in Cheshire, United Kingdom, has shown that the unique features of this new Geranium are stable and reproduced true to type in successive generations.

SUMMARY OF THE INVENTION

Plants of the cultivar Ravpil have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Ravpil'. These characteristics in combination distinguish 'Ravpil' as a new and distinct cultivar:

1. Medium green leaf color.
2. Mounded and prostrate growth habit.
3. Dark purple-colored flowers.

BRIEF DESCRIPTION OF THE PHOTOGRAPHS

The accompanying colored photographs illustrate the overall appearance of the new Geranium, showing the colors as true as it is reasonably possible to obtain in colored reproductions of this type. Colors in the photographs may differ slightly from the color values cited in the detailed botanical description which more accurately describe the actual colors of the new Geranium.

The photograph on the first sheet comprises a top perspective view of a typical flowering plant of 'Ravpil' grown in the field.

The photograph at the top of the second sheet is a close-up view of a typical plant of 'Ravpil'.

The photograph at the bottom of the second sheet is a close-up view of a typical open flower and a typical leaf of 'Ravpil'.

DETAILED BOTANICAL DESCRIPTION

In the following description, color references are made to The Royal Horticultural Society Colour Chart except where general terms of ordinary dictionary significance are used. Plants used for the following description were about 30 weeks old and grown in the field conditions which closely approximate commercial production conditions during the spring and summer in Cheshire, United Kingdom.

Botanical classification: *Geranium cinereum* cultivar Ravpil.

Parentage: Naturally-occurring whole plant mutation of *Geranium cinereum* cultivar Laurence Flatman, not patented.

Propagation:

*Type cutting.*—By cuttings.

*Time to initiate roots.*—About 21 to 28 days at 18° C.

*Time to produce a rooted liner.*—About 90 days at 18° C.

*Root description.*—Thick in diameter.

Plant description:

*Form.*—Perennial flowering plant; mounding and prostrate. Appropriate for 17-cm containers.

*Crop time.*—After rooting, about 20 to 30 weeks are required to produce finished flowering plants in 17-cm containers.

*Plant height.*—About 15 cm.

*Plant diameter.*—About 35 cm.

*Vigor.*—Moderate to vigorous.

*Foliage description.*—Leaves basal, simple, generally symmetrical, and long-persisting. Length: About 3 cm. Width: About 3.5 cm. Shape: Palmately lobed. Apex: Acute. Base: Sagittate. Margin: Deeply serrate to incised. Texture: Both surfaces pubescent. Fragrance: Faint spicy fragrance when rubbed, pleasant. Petiole: Length: About 9 cm. Diameter: About 1.2 mm. Color: Young foliage, upper surface: 137A to 137B. Young foliage, lower surface: 137D. Mature foliage, upper surface: 137B; veins, 137A. Mature foliage, lower surface: 137D; veins, 137D. Petiole: 144A to 145A.

Flower description:

*Appearance*.—Single rounded cup-shaped flowers with five petals. Flowering stems arise from the plant base. Flowers not persistent.

*Quantity of flowers*.—About 8 flowers per flowering stem.

*Natural flowering season*.—Summer in the Netherlands; flowering continuous.

*Fragrance*.—None detected.

*Flower longevity*.—About 3 days.

*Flower size*.—Length: About 2.8 cm. Diameter: About 1 cm.

*Flower buds* (*before showing color*).—Length: About 8 mm. Diameter: About 5 mm. Shape: Obovate. Color: 191A to 191B.

*Petals*.—Length: About 1.3 cm. Width: About 1 cm. Shape: Obcordate; apex, retuse; margin, entire with short hairs. Texture: Somewhat rugose. Color: When opening, upper surface: 71A; veins slightly darker than 71A. When opening, lower surface: 70A to 70B. Fully opened, upper surface: 71B; veins darker than 71A. Fully opened, lower surface: 70B to 72B.

*Sepals*.—Quantity: Five. Calyx length: About 6 mm. Calyx diameter: About 1.5 cm. Shape: Oval to oblong; apex, mucronate; margin, entire. Texture: Pubescent. Color: Upper surface: 141A to 141B. Lower surface: 191B.

*Pedicel*.—Length: About 2.5 cm. Angle: About 30 to 40° from vertical. Strength: Moderate to weak. Color: 144A to 145A.

*Peduncle*.—Length: About 15 cm. Diameter: About 1.5 mm. Aspect: Mostly upright or outwardly angled. Texture: Pubescent. Color: 144A to 145A.

*Reproductive organs*.—Stamens: Quantity: Ten. Anther shape: Ovate to oblong; dorsifixed. Anther length: About 2.5 mm. Anther color: Purple. Pollen amount: Scarce. Pistils: Quantity: Five. Pistil length: About 8 mm. Style length: About 6 mm. Style color: 144A to 145A. Stigma color: 187A to 187B. Ovary color: 144A to 145A.

*Seed description*.—Seed development has not been observed.

Disease resistance: Plants of the new Geranium have been noted to be resistant to pathogens common to Geranium.

It is claimed:

1. A new and distinct cultivar of Geranium plant named 'Ravpil', as illustrated and described.

* * * * *

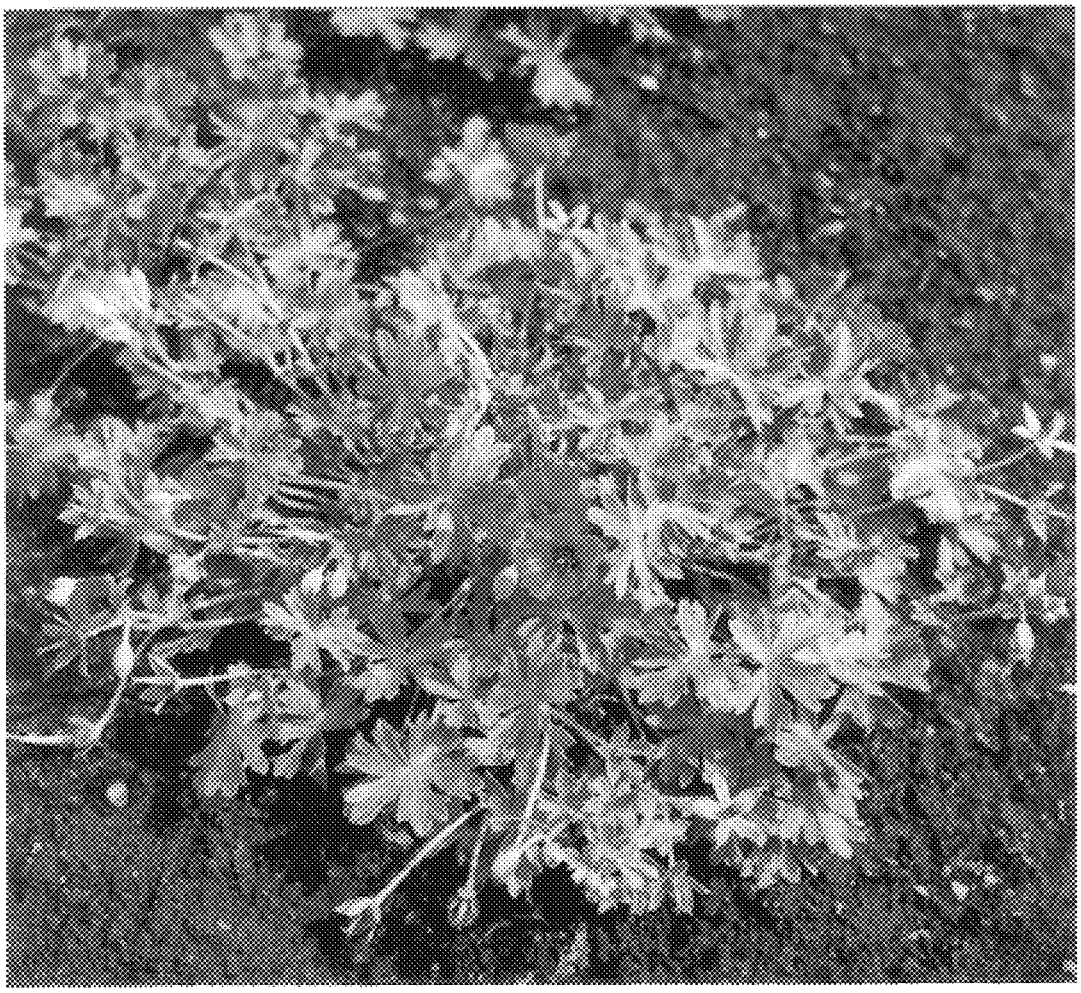

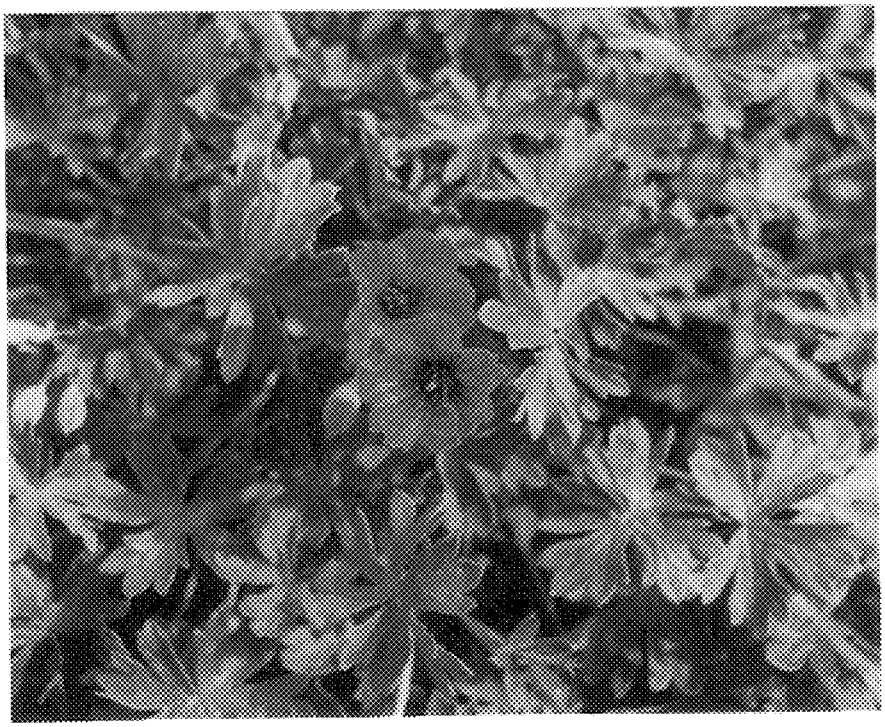
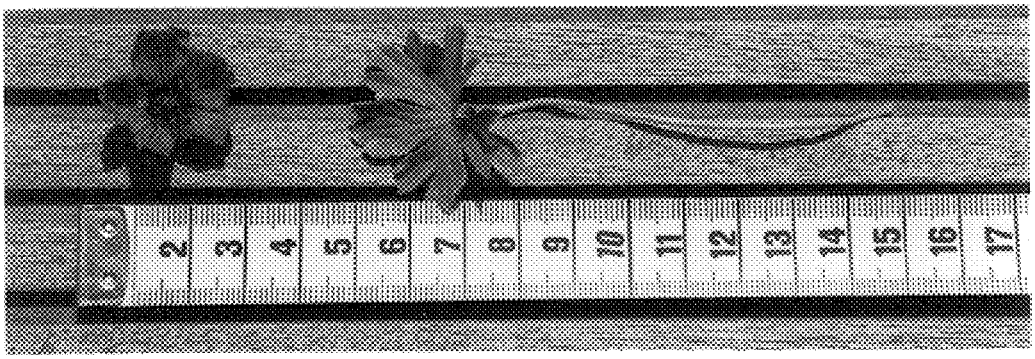
0
2
3
4
5
6
7
8
9
10
11
12
13
14
15
16
17